(12) United States Patent
Sumida et al.

(10) Patent No.: US 7,232,917 B2
(45) Date of Patent: Jun. 19, 2007

(54) CYCLIC FLUORINE COMPOUNDS, POLYMERIZABLE FLUOROMONOMERS, FLUOROPOLYMERS, AND RESIST MATERIALS CONTAINING THE FLUOROPOLYMERS AND METHOD FOR PATTERN FORMATION

(75) Inventors: Shinichi Sumida, Kawagoe (JP); Haruhiko Komoriya, Kawagoe (JP); Kazuhiko Maeda, Kawagoe (JP)

(73) Assignee: Central Glass Company, Limited, Yamaguci (JP)

( * ) Notice: Subject to any disclaimer, the term of this patent is extended or adjusted under 35 U.S.C. 154(b) by 0 days.

(21) Appl. No.: 10/563,557

(22) PCT Filed: Jul. 1, 2004

(86) PCT No.: PCT/JP2004/009680

§ 371 (c)(1),
(2), (4) Date: Jun. 27, 2006

(87) PCT Pub. No.: WO2005/005404

PCT Pub. Date: Jan. 20, 2005

(65) Prior Publication Data

US 2006/0270864 A1    Nov. 30, 2006

(30) Foreign Application Priority Data

Jul. 9, 2003    (JP) .............................. 2003-272269

(51) Int. Cl.
 C07D 305/14    (2006.01)
 C08G 65/22    (2006.01)
 C23F 1/42    (2006.01)
(52) U.S. Cl. .......................... 549/511; 528/402; 216/42
(58) Field of Classification Search ................. 549/511; 528/402; 216/42
See application file for complete search history.

(56) References Cited

FOREIGN PATENT DOCUMENTS

| JP | 2002-145962 | 5/2002 |
| JP | 2002-206012 | 7/2002 |
| JP | 2002-275215 | 9/2002 |
| JP | 2002-327013 | 11/2002 |
| JP | 2002-338633 | 11/2002 |
| JP | 2002-350179 | 12/2002 |
| WO | WO 01/98834 | 12/2001 |

OTHER PUBLICATIONS

Kodama et al., "Synthesis of Novel Fluoropolymer for 157 nm Photoresists by Cyclo-polymerization", Proceedings of SPIE, vol. 4690, 2002, pp. 76-83.

*Primary Examiner*—Bernard Dentz
(74) *Attorney, Agent, or Firm*—Young & Thompson

(57) ABSTRACT

The present invention provides a fluorine-containing cyclic compound represented by general formula (1):

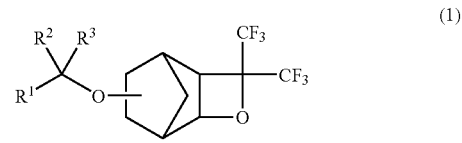

(1)

wherein $R^1$ represents a halogen atom, and $R^2$ and $R^3$ each represents hydrogen or a hydrocarbon group. The above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom or a sulfur atom. Further, a fluorine-containing polymerizable monomer derived from the above-mentioned fluorine-containing cyclic compound, a fluorine-containing polymer compound obtained by polymerization or copolymerization using the above-mentioned compound or monomer, further a resist material and a pattern forming process using the above-mentioned polymer compound are also disclosed. According to the invention, there is provided the polymer compound suitable for a resist material having high transparency in a wide wavelength region from an ultraviolet region to a near-infrared light region, high adhesion to a substrate, film forming properties, high etching resistance and a high glass transition point at once, particularly for a photoresist material in a vacuum ultraviolet wavelength region. Further, the pattern forming process using the polymer compound is suitable for the formation of a high-resolution pattern form.

15 Claims, 2 Drawing Sheets

CYCLIC FLUORINE COMPOUNDS, POLYMERIZABLE FLUOROMONOMERS, FLUOROPOLYMERS, AND RESIST MATERIALS CONTAINING THE FLUOROPOLYMERS AND METHOD FOR PATTERN FORMATION

TECHNICAL FIELD

The present invention relates to a novel fluorine-containing cyclic compound, fluorine-containing polymerizable monomer and fluorine-containing polymer compound, and further to a resist material and a pattern forming process in a vacuum ultraviolet wavelength region using the same.

BACKGROUND ART

Fluorine-containing compounds have been continuously used or developed in wide application fields centering on the field of advanced materials from characteristics of fluorine such as water repellency, oil repellency, low water absorption, heat resistance, weather resistance, corrosion resistance, transparency, photosensitivity, low refractive index properties and low dielectric property. In particular, when the characteristics of transparency behavior in each wavelength are utilized, they are used in the coating field. Active researches and developments have been made in the fields of anti-reflection films to which low refractive index properties and transparency of visible light are applied, optical devices to which transparency in a long wavelength band (an optical communication wavelength band) is applied, resist compositions to which transparency in an ultraviolet region (particularly, a vacuum ultraviolet region) is applied, and the like. Recent researches of resist materials have shifted from 248-nm KrF to resists for 193-nm ArF excimer lasers or $F_2$ lasers of the vacuum ultraviolet region represented by 157 nm, and resist materials containing polymer compounds into which acid labile groups are incorporated have been generally designed, the solubility in an alkaline aqueous solution of the acid labile groups being changed by the action of acids.

As the acid labile groups, there are in heavy usage at present a methoxymethyl group, a tert-butyl group and a tert-butyloxycarbonyl group. The resist materials containing those acid labile groups have disadvantages of being large in the outgas amount after exposure, further, not being excellent in resistance to a dry etching gas and transparency in each wavelength, having a low glass transition point, and the like. Specifically, as acidic groups for 157 nm, there have been developed trifluoromethylmethacrylic acid, a hexafluorocarbinol group and a fluorine-containing acidic group such as a fluorine-containing cyclic alcohol. When acid labile groups for protecting those acidic groups are a methoxymethyl group, a tert-butyl group and a tert-butyloxycarbonyl group, there arise the disadvantages of decreasing in etching resistance, decreasing in glass transition point (Tg) and forming an outgas in large amounts, because no ring structure is contained in the acid labile groups. Further, no fluorine atom is contained, so that it has also been impossible to improve transparency. Recently, it has been reported that the use of cyclic hydrocarbon group-containing acid labile groups can improve dry etching resistance (for example, see non-patent document 1). However, adhesion and transparency decrease to the content of the acid labile groups, because of their hydrophobic cyclohexane structure. Consequently, there has been desired the creation of acid labile groups which improve dry etching resistance, enhance transparency in each wavelength used and adhesion to a substrate, and realize a high glass transition point.

Non-Patent Document: S. Kodama, et al., Proceedings of SPIE—The International Society for Optical Engineering (2002), 4690, 76–83

DISCLOSURE OF THE INVENTION

An object of the invention is to provide an acid labile group having high transparency in a wide wavelength region from an ultraviolet region to a near-infrared light region, high adhesion to a substrate, film forming properties, high etching resistance and a high glass transition point at once, a fluorine-containing compound using the same, a fluorine-containing polymer compound, a resist material and a pattern forming process.

In order to solve the above-mentioned problems, the present inventors have conducted intensive studies. As a result, there has been discovered a novel fluorine-containing cyclic compound which can be derived from norbornadiene and hexafluoroacetone via several steps, and has a high fluorine content and an oxacyclobutane ring. It has been discovered that the fluorine-containing cyclic compound has high transparency in the wide wavelength region from the ultraviolet region to the near-infrared light region due to its high fluorine content, is enhanced in adhesion to the substrate and film forming properties, because an unshared electron pair of an endocyclic oxygen atom of the oxacyclobutane ring projects out of the ring, and has high etching resistance and a high glass transition point due to its polycyclic structure. The fluorine-containing polymer compound obtained by polymerization or copolymerization using a polymerizable monomer into which the fluorine-containing cyclic compound is introduced as the acid labile group has been applied to a resist material, and a pattern forming process using the same has been discovered, thus resulting in the completion of the invention.

That is, the invention relates to the following constitutions:

1) A fluorine-containing cyclic compound represented by general formula (1):

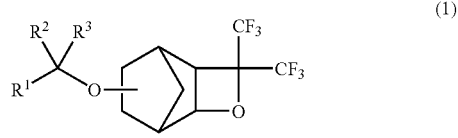

In general formula (1), $R^1$ represents a halogen atom, and $R^2$ and $R^3$ each represents hydrogen or a hydrocarbon group. The above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom or a sulfur atom.

2) The fluorine-containing cyclic compound described in the above item 1), which is represented by structural formula (2):

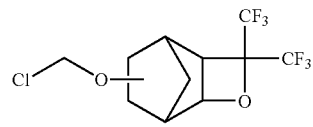
(2)

3) A fluorine-containing cyclic compound derived from the fluorine-containing cyclic compound described in the above item 1) or 2), which is represented by general formula (3):

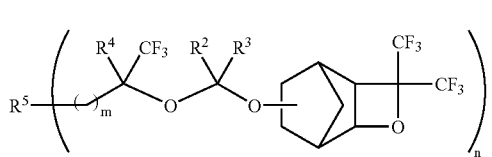
(3)

In general formula (3), $R^2$ and $R^3$ each represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom or a sulfur atom. $R^4$ and $R^5$ each represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom, a sulfur atom, a carbonyl bond or a double bond. Further, $R^5$ may be bonded to any polymer chain. n represents 1 to 5, and m represents 0 to 5.

4) A fluorine-containing cyclic compound derived from the fluorine-containing cyclic compound described in the above item 1) or 2), which is represented by general formula (4):

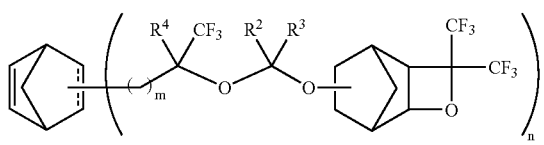
(4)

In general formula (4), $R^2$ and $R^3$ each represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom or a sulfur atom. $R^4$ represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom, a sulfur atom or a carbonyl bond. n represents 1 to 5, and m represents 0 to 5.

5) A fluorine-containing cyclic compound represented by structural formula (5):

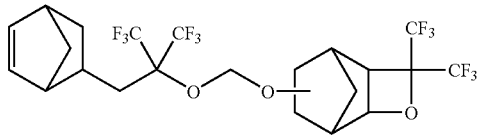
(5)

6) A fluorine-containing cyclic compound derived from the fluorine-containing cyclic compound described in the above item 1) or 2), which is represented by general formula (6):

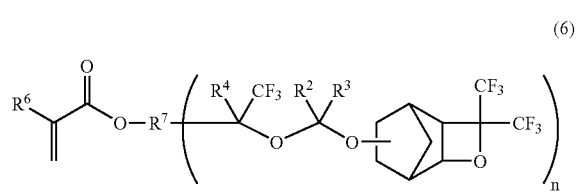
(6)

In general formula (6), $R^2$ and $R^3$ each represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom or a sulfur atom. $R^4$ represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom, a sulfur atom or a carbonyl bond. $R^6$ represents hydrogen, a fluorine atom, a halogen atom, an alkyl group or a halogenated alkyl group. n represents 1 to 5. $R^7$ is a methylene group, a methine group, or a cyclic hydrocarbon group or aromatic hydrocarbon group represented by structural formulas (7) to (9), which may contain a halogen atom, an oxygen atom, a nitrogen atom or a sulfur atom as a substituent group thereof. In structural formula (7), m represents 0 to 5.

(7)

(8)

(9)

7) A fluorine-containing cyclic compound derived from the fluorine-containing cyclic compound described in the above item 1) or 2), which is represented by general formula (10):

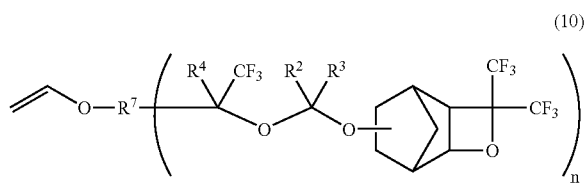

In general formula (10), $R^2$ and $R^3$ each represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom or a sulfur atom. $R^4$ represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom, a sulfur atom or a carbonyl bond. n represents 1 to 5. $R^7$ is a methylene group, a methine group, or a cyclic hydrocarbon group or aromatic hydrocarbon group represented by structural formula (7) to (9), which may contain a halogen atom, an oxygen atom, a nitrogen atom or a sulfur atom as a substituent group thereof. In structural formula (7), m represents 0 to 5.

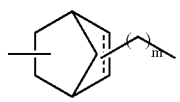

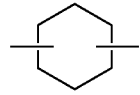

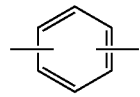

8) A fluorine-containing cyclic compound derived from the fluorine-containing cyclic compound described in the above item 1) or 2), which is represented by general formula (11):

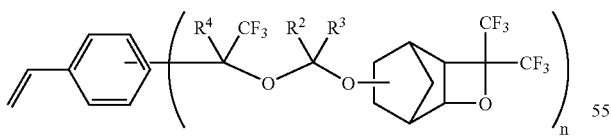

In general formula (11), $R^2$ and $R^3$ each represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom or a sulfur atom. $R^4$ represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom, a sulfur atom or a carbonyl bond. n represents 1 to 5.

9) A fluorine-containing cyclic compound derived from the fluorine-containing cyclic compound described in the above item 1) or 2), which is represented by general formula (12):

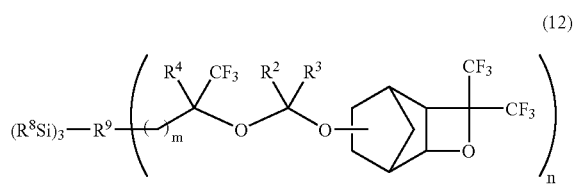

In general formula (12), $R^2$ and $R^3$ each represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom or a sulfur atom. $R^4$ represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom, a sulfur atom or a carbonyl bond. $R^8$ represents a halogen atom or an alkoxy group. n represents 1 to 5, and m represents 0 to 5. $R^9$ is a cyclic hydrogen group represented by structural formulas (7) and (8) or an aromatic hydrocarbon group, which may contain a halogen atom, an oxygen atom, a nitrogen atom or a sulfur atom as a substituent group thereof.

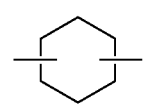

10) A fluorine-containing cyclic compound derived from the fluorine-containing cyclic compound described in the above item 1) or 2), which is represented by general formula (13):

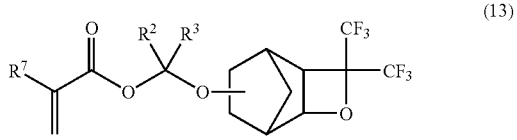

In general formula (13), $R^2$ and $R^3$ each represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom or a sulfur atom. $R^7$ represents hydrogen, a fluorine atom, a halogen atom, an alkyl group or a halogenated alkyl group.

11) A fluorine-containing cyclic compound represented by structural formula (14):

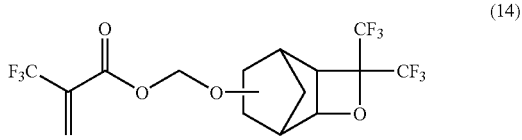

12) A fluorine-containing polymer compound obtained by polymerization or copolymerization using the fluorine-containing cyclic compound described in any one of the above items 3) to 11).

13) A fluorine-containing polymer obtained by reacting a polymer containing one or more functional groups selected from a carboxyl group, a hydroxyl group, a hexafluorocarbinol group, an amino group and a sulfonic acid with the fluorine-containing cyclic compound described in the above item 1) or 2).

14) A resist material using the fluorine-containing polymer compound described in the above item 12) or 13).

15) A pattering process using the resist material described in the above item 14).

BEST MODE FOR CARRYING OUT THE INVENTION

Figure 1:
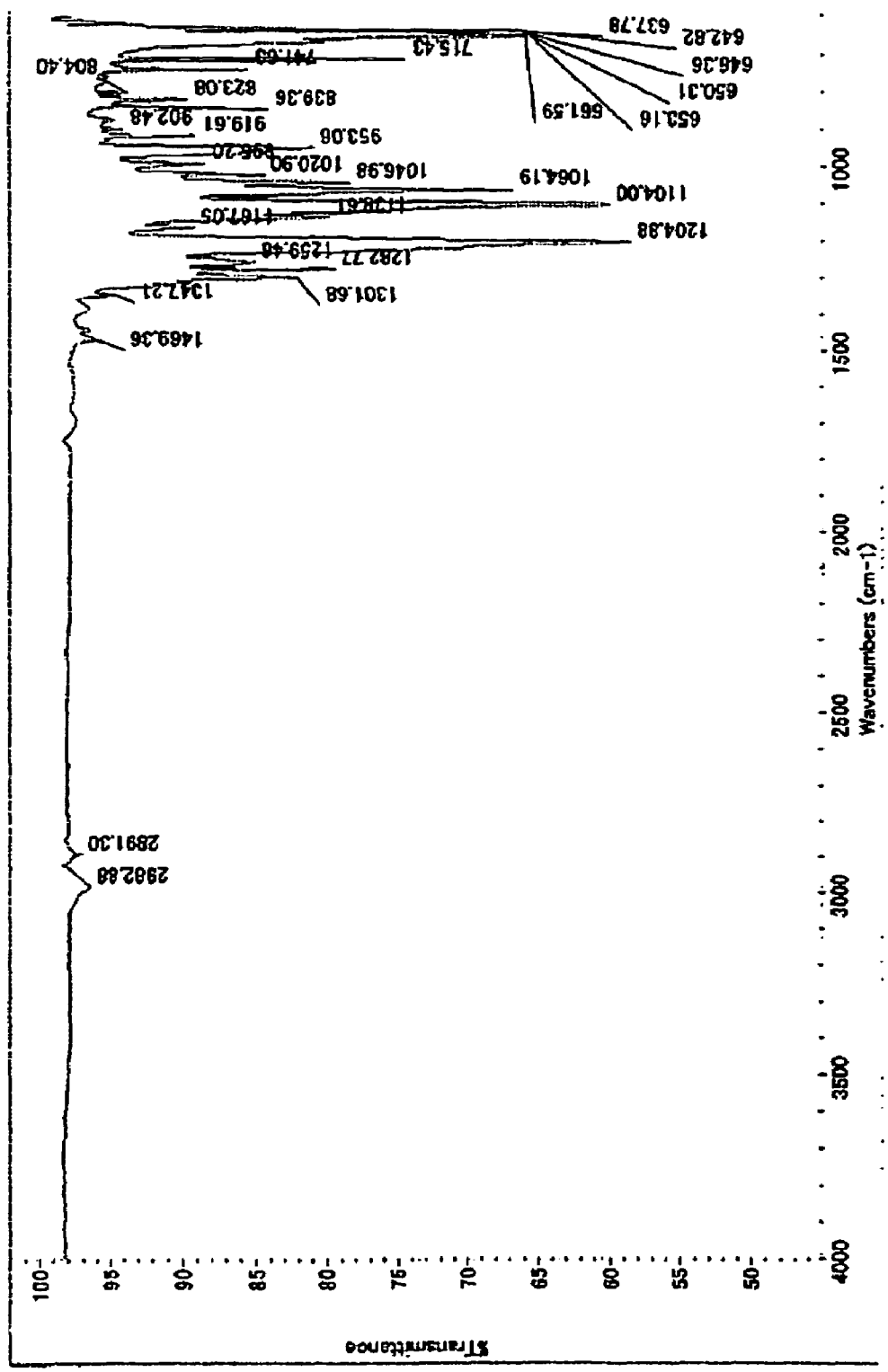
FIG. 1 is a diagram showing an IR spectrum as physical property data of Example 1.

The fluorine-containing cyclic compound of the invention will be illustrated below. The compound of the invention represented by general formula (1) is a compound having an oxacyclobutane structure derived from norbornadiene and hexafluoroacetone, and a novel fluorine-containing cyclic compound having transparency due to fluorine, adhesion due to cyclic oxygen, and etching resistance, an increase in glass transition point (Tg) and an outgas reduction function due to a polycyclic structure, having no acidic group having solubility, and acting as an acid labile group.

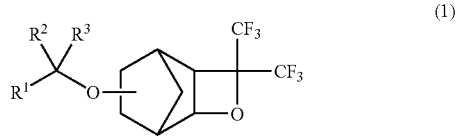

In general, it is known that an increase in transparency in a wide wavelength region from an ultraviolet region to a near-infrared light region is induced with an increase in fluorine content. On the other hand, a decrease in adhesion to a substrate and a decrease in film forming properties are also induced with an increase in fluorine content. However, the compound indicated in general formula (1) has made it possible to enhance adhesion to the substrate and film forming properties, because an unshared electron pair of an endocyclic oxygen atom of the oxacyclobutane structure projects out of the ring, to improve etching resistance by the polycyclic structure and further to increase the glass transition point.

In the compound indicated in general formula (1) according to the invention, $R^1$ represents a halogen atom, and $R^2$ and $R^3$ each represent hydrogen or a hydrocarbon group. The above-mentioned hydrocarbon group is a straight-chain, branched or cyclic hydrocarbon group having 1 to 25 carbon atoms or an aromatic hydrocarbon group, and may contain a halogen atom, an oxygen atom, a nitrogen atom or a sulfur atom. However, from the occurrence of a decrease in transparency and an increase in the refractive index, it is preferred that the carbon number is from 1 to 5. Examples thereof include a methyl group, an ethyl group, a n-propyl group, an iso-propyl group, a n-butyl group, a sec-butyl group, a tert-butyl group and the like. Further, in order to improve transparency, they may be hydrocarbon groups in which hydrogen atoms of those functional groups are partially or totally substituted by fluorine atoms.

The compound of the invention represented by general formula (3) can be derived from the fluorine-containing cyclic compound represented by general formula (1) or structural formula (2).

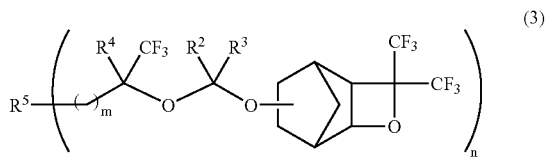

In the compound represented by general formula (3), $R^2$ and $R^3$ are the same as exemplified as $R^2$ and $R^3$ contained in general formula (1) or structural formula (2). $R^4$ and $R^5$ each represents hydrogen or a hydrocarbon group, and the above-mentioned hydrocarbon group is a straight-chain, branched or cyclic hydrocarbon group having 1 to 25 carbon atoms or an aromatic hydrocarbon group, and may contain a halogen atom, an oxygen atom, a carbonyl bond or a double bond. Further, $R^5$ may be bonded to any polymer chain. Furthermore, n represents 1 to 5, and m represents 0 to 5.

Methods for synthesizing a polymer compound from the polymer compound represented by general formula (3). The first method is a method of introducing a monomer having a polymerizable functional group into the position of $R^5$ to introduce the structure of general formula (1) or (2) into a polymer compound by polymerization reaction thereof, thereby synthesizing the polymer compound. The second method is a method of reacting the compound of general formula (1) or (2) with an acidic group such as a carboxylic acid, a phenol, a hexafluorocarbinol or a fluorine-containing cyclic alcohol group in a polymer compound, thereby introducing general formula (1) or (2) into the polymer compound.

First, the first method will be described. When used as a polymeric material obtained by polymerization reaction, a decrease in polymerizability caused by steric hindrance, a decrease in transparency and an increase in the refractive index occur with an increase in the carbon number of a substituent group. Accordingly, the carbon number of $R^4$ is more preferably from 1 to 5. Examples thereof include a methyl group, an ethyl group, a n-propyl group, a n-butyl group and the like. In order to improve transparency, there may be used a monofluoromethyl group, a difluoromethyl group, a trifluoromethyl group and the like obtained by partially or totally substituting hydrogen atoms of those functional groups by fluorine atoms. Further, an oxygen atom, a carbonyl bond or a double bond may be contained. Examples of the polymerizable functional groups which can be used in $R^5$ include a vinyl group, an acrylic group, an acryloyl group, a methacryloyl group, a fluorovinyl group, a difluorovinyl group, a trifluorovinyl group, a difluorotrifluoromethylvinyl group, a trifluoroallyl group, a perfluoroallyl group, trifluoromethylacryloyl group, a nonylfluorobutylacryloyl group, a vinyl ether group, a fluorine-containing vinyl ether group, an allyl ether group, a fluorine-containing allyl ether group, a styryl group, a fluorine-containing styryl group, a norbornyl group, a fluorine-containing norbornyl group, a silyl group and the like. an acryloyl group, a methacryloyl group, trifluoromethylacryloyl group, a vinyl ether group and a norbornyl group can be suitably used from their high polymerization reactivity and high copolymerization reactivity with another monomer. One having a fluorine atom in the functional group is applied in order to further impart transparency and low refractive index properties.

The polymer compound of the first method means a polymer compound obtained by homopolymerizing or copolymerizing the compound indicated by general formula (3), which has the above-mentioned polymerizable functional group. Monomers copolymerizable therewith are not particularly limited, as long as they have copolymerization reactivity, and specifically, preferred is copolymerization with one or more kinds of monomers selected from maleic anhydride, an acrylic ester, a fluorine-containing acrylic ester, a methacrylic ester, a fluorine-containing methacrylic ester, a styrenic compound, a fluorine-containing styrenic compound, a vinyl ether, a fluorine-containing vinyl ether, an allyl ether, a fluorine-containing allyl ether, an olefin, a fluorine-containing olefin, a norbornene compound, a fluorine-containing norbornene compound, sulfur dioxide, a vinylsilane and fluorine-containing vinyl sulfone.

Then, the second method which can be used in the invention will be described. The target material of the second method is a compound in which $R^5$ indicated in general formula (3) is bonded to any polymer chain. That is, the polymer compound which can be used in the second method corresponds to a method of previously imparting into the polymer a carboxyl group, a phenol group, a hexafluorocarbinol group, a fluorine-containing cyclic alcohol group or the like which acts as an acidic group, and reacting the polymer compound with the compound of general formula (1) or (2) in an organic solvent solution under the presence of a base to protect the above-mentioned acidic group, thereby obtaining the target polymer compound.

The acidic group-containing polymeric polymer which can be used in the invention will be described herein. Polymerizable monomers which can be used are no particularly limited by their structure, as long as they have the acidic groups already enumerated, and specifically, they are acrylic acid, methacrylic acid, fluorine-containing acrylic acid, fluorine-containing methacrylic acid, fluoroacrylic acid, trifluoromethylacrylic acid, nonylfluorobutylacrylic acid, a carboxyl group-containing norbornene, an acrylic ester having an hexafluorocarbinol or another fluorine-containing alcohol at a side chain terminal thereof, a fluorine-containing acrylic ester, a vinyl ether, an allyl ether, a cyclic olefin, styrene, a norbornene and the like. Copolymerizable monomers which can be used are not particularly limited, and the monomers and copolymerization components which can be used in the first method are also suitably employed as monomers in the second method without exception.

As for the acid labile group content in the polymer compound, it is only required that the acid labile group is contained in an amount sufficient to insolubilize the polymer in any alkali solution. Specifically, there can be used the polymer compound into which the acid labile group is introduced at a ratio of 5 mol % to 100 mol % based on the acidic group of the polymer.

The role of the base used in this reaction is to capture an acid generated in the reaction system, or to allow it to act on the acidic group of the polymer to form an alkoxide salt. In the invention, both of an inorganic base and an organic base can be used, and examples thereof include inorganic salts such as sodium hydroxide, sodium carbonate, sodium hydrogen carbonate, potassium hydroxide, potassium carbonate, potassium hydrogen carbonate, sodium hydride, sodium methoxide, sodium ethoxide, sodium tert-butoxide and potassium tert-butoxide, and organic bases such as triethylamine, diethylamine, piperidine, pyrrolidine and 1,8-diazabicyclo[5,4,0]-7-undecene. In particular, potassium carbonate, sodium hydride, triethylamine and diethylamine are used, and used in an amount of 1 to 10 moles, preferably 1 to 3 moles, based on mole of the acidic group of the polymer.

The solvent can be used with no particular limitation, as long as it does not take part in the reaction and dissolves the polymer compound, and there can be exemplified hydrocarbons such as benzene and toluene, ethers such as diethyl ether, tetrahydrofuran and dioxane, halogenated hydrocarbons such as dichloromethane and chloroform, alkyl ketones such as acetone, alcohols such as methanol and ethanol, aprotic polar solvents such as acetonitrile, N,N-dimethylformamide, dimethyl sulfoxide and hexamethylphosphoric triamide, and the like. These may be used either alone or as a mixture of two or more thereof.

Although the reaction temperature is not particularly limited, the reaction is usually possible within the range of 0° C. to 200° C., and it is preferably from 0° C. to 50° C. Although treatment after the reaction is not particularly limited, a method is possible in which after a reaction solution has been added to water or ice water, a polymer precipitated is dissolved in an organic solvent, followed by reprecipitation with a solvent such as hexane, filtration and drying, and the target material is taken out.

The fluorine-containing cyclic compound of the invention represented by general formula (6) is a compound derived from the fluorine-containing cyclic compound described in any one of general formula (1) and structural formula (2).

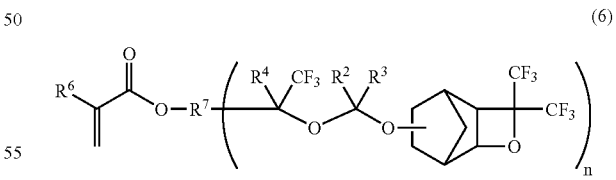

(6)

In general formula (6), $R^1$ to $R^4$ are the same as exemplified in general formula (1), structural formula (2) or general formula (3), and $R^6$ represents hydrogen, a fluorine atom, a halogen atom, an alkyl group or a halogenated alkyl group. n represents 1 to 5. $R^7$ is a methylene group, a methine group, or a cyclic hydrocarbon group or aromatic hydrocarbon group represented by structural formulas (7) to (9), which may contain a halogen atom, an oxygen atom, a nitrogen atom or a sulfur atom as a substituent group thereof. In structural formula (7), m represents 0 to 5.

(7)

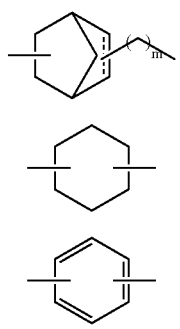

(8)

(9)

$R^6$ includes hydrogen, a fluorine atom, a methyl group, an ethyl group, a n-propyl group, n-butyl group and the like. The halogenated alkyl group is a functional group in which hydrogen atoms of an alkyl group are partially or totally substituted by halogen atoms, and a monofluoromethyl group, a difluoromethyl group, a trifluoromethyl group and a nonylfluorobutyl group can be exemplified. $R^7$ is a methylene group, a methine group, a cyclic hydrocarbon group or an aromatic hydrocarbon group, and may be a cyclic hydrocarbon group or aromatic hydrocarbon group in which hydrogen atoms of the functional group are partially or totally substituted by fluorine atoms, in order to improve transparency. Further, it may contain a halogen atom, an oxygen atom, a nitrogen atom or a sulfur atom.

The fluorine-containing cyclic compound of the invention represented by general formula (12) is a compound derived from the fluorine-containing cyclic compound described in any one of general formula (1) and structural formula (2).

(12)

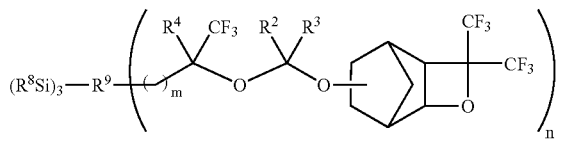

In general formula (12), $R^1$ to $R^4$ are the same as exemplified in general formula (1), structural formula (2) or general formula (3), and $R^8$ represents a halogen atom or an alkoxy group. $R^9$ is a cyclic hydrocarbon group represented by structural formulas (7) and (8) or an aromatic hydrocarbon group, which may contain a halogen atom, an oxygen atom, a nitrogen atom or a sulfur atom as a substituent group thereof. In structural formula (7), m represents 0 to 5.

(7)

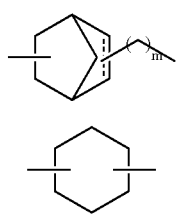

(8)

As $R^8$, there can be exemplified halogen atoms such as a fluorine atom, a chlorine atom, a bromine atom and an iodine atom, and alkoxy groups such as a methoxy group, an ethoxy group, a n-propoxy group, an iso-propoxy group and a n-butoxy group. $R^9$ is a cyclic hydrocarbon group or an aromatic hydrocarbon group. However, in order to improve transparency, it may be a cyclic hydrocarbon group or aromatic hydrocarbon group in which hydrogen atoms of the functional group are partially or totally substituted by fluorine atoms.

The polymer compound according to the invention will be described below. The polymer compound of the invention means a polymer compound obtained by homopolymerizing or copolymerizing of the fluorine-containing cyclic compound indicated by any one of structural formulas (1) to (14).

Monomers copolymerizable with the fluorine-containing cyclic compound of the invention are not particularly limited, as long as they have copolymerization reactivity, and specifically, preferred is copolymerization with one or more kinds of monomers selected from maleic anhydride, an acrylic ester, a fluorine-containing acrylic ester, a methacrylic ester, a fluorine-containing methacrylic ester, a styrenic compound, a fluorine-containing styrenic compound, a vinyl ether, a fluorine-containing vinyl ether, an allyl ether, a fluorine-containing allyl ether, an olefin, a fluorine-containing olefin, a norbornene compound, a fluorine-containing norbornene compound, sulfur dioxide, a vinylsilane and fluorine-containing vinyl sulfone.

The acrylic ester or methacrylic ester which can be used in the invention can be used with no particular limitation with respect to its ester side chain. When known compounds thereof are exemplified, there can be used an alkyl ester of acrylic acid or methacrylic acid such as methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylhexyl acrylate or methacrylate, lauryl acrylate or methacrylate, 2-hydroxyethyl acrylate or methacrylate, or 2-hydroxypropyl acrylate or methacrylate; an acrylate or methacrylate containing an ethylene glycol, propylene glycol or tetramethylene glycol group; further, an unsaturated amide such as acrylic amide, methacrylic amide, N-methylolacrylic amide, N-methylolmethacrylic amide or diacetoneacrylic amide; acrylonitrile; an alkoxysilane-containing vinylsilane; an alkoxysilane-containing acrylic or methacrylic ester; tert-butyl acrylate or methacrylate; 3-oxocyclohexyl acrylate or methacrylate; adamantyl acrylate or methacrylate; an alkyladamantyl acrylate or methacrylate; cyclohexyl acrylate or methacrylate; tricyclodecanyl acrylate or methacrylate; an acrylate or methacrylate having a cyclic structure such as a lactone ring or a norbornene ring; acrylic acid; methacrylic acid; and the like. Further, it is also possible to co-mplymerize the above-mentioned acrylate compound containing a cyano group at the α-position, or maleic acid, fumaric acid or maleic anhydride as an analogous compound.

Further, as the fluorine-containing acrylic ester or fluorine-containing methacrylic ester which can be used in the invention, a monomer containing a fluorine atom or a fluorine atom-containing group at the acrylic α-position, or a fluorine-containing compound which is an acrylic ester or methacrylic ester comprising a substituent group containing a fluorine atom at the ester moiety and contains fluorine at both the α-position and the ester moiety are also suitable. Furthermore, a cyano group may be introduced into the α-position. For example, as the monomer in which fluorine is introduced into the α-position, suitably employed is a monomer in which fluorine, a trifluoromethyl group, a trifluoroethyl group, a nonafluoro-n-butyl group or the like is imparted to the α-position of the above-mentioned non-fluorine-containing acrylic ester or methacrylic ester. In that case, fluorine is not necessarily required to be contained in the ester moiety. When an α-trifluoromethylacrylic alkyl ester is used as a copolymerization component, the yield of the polymer is relatively high, and the polymer obtained has good solubility in an organic solvent. This is therefore preferably employed.

On the other hand, the monomer containing fluorine at the ester moiety thereof is an acrylic ester or methacrylic ester having a unit which has a fluorine alkyl group, a perfluoroalkyl group or a fluoroalkyl group, at the ester moiety, or a cyclic structure and an fluorine atom coexisting at the ester moiety, and which has a fluorine-containing benzene ring, a fluorine-containing cyclopentane ring, a fluorine-containing cyclohexane ring, a fluorine-containing cycloheptane ring or the like in which the cyclic structure is substituted, for example, by a fluorine atom, a trifluoromethyl group, a hexafluorocarbinol group or the like. Further, an acrylic ester or methacrylic ester in which the ester moiety is a fluorine-containing t-butyl ester group is also usable. It is also possible to use monomers in which these fluorine-containing functional groups are used in combination with the fluorine-containing alkyl group at the α-position. Particularly typical examples of such units in the monomer form include 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate, perfluorocyclohexylmethyl methacrylate, 6-[3,3,3-trifluoro-2-hydroxy-2-(trifluoromethyl)propyl]bicyclo[2.2.1]heptyl-2-yl acrylate, 6-[3,3,3-trifluoro-2-hydroxy-2-(trifluoromethyl)propyl]bicyclo[2.2.1]heptyl-2-yl 2-(trifluoromethyl)acrylate, 6-[[3,3,3-trifluoro-2-hydroxy-2-(trifluoromethyl)propyl]bicyclo 2.2.1]heptyl-2-yl methacrylate, 1,4-bis(1,1,1,3,3,3-hexafluoro-2-hydroxyisopropyl)cyclohexyl acrylate, 1,4-bis (1,1,1,3,3,3-hexafluoro-2-hydroxyisopropyl)cyclohexyl methacrylate, 1,4-bis(1,1,1,3,3,3-hexafluoro-2-hydroxyisopropyl)cyclohexyl 2-trifluoromethyl acrylate and the like.

Further, as the styrenic compound or fluorine-containing styrenic compound which can be used in the invention, there can be used a compound to which one or a plurality of functional groups which have modified hexafluorocarbinol groups or hydroxyl groups thereof are bonded, as well as styrene, fluorinated styrene or hydroxystyrene. That is, it is possible to preferably use styrene or hydroxystyrene in which hydrogen is substituted by a fluorine atom or a trifluoromethyl group, the above-mentioned styrene in which halogen, an alkyl group or a fluorine-containing alkyl group is bonded to the α position, perfluorovinyl group-containing styrene, and the like.

Furthermore, as the vinyl ether, the fluorine-containing vinyl ether, the allyl ether or the fluorine-containing allyl group, there can be used an alkylvinyl ether, an alkylallyl ether or the like which may contain a methyl group, an ethyl group, a propyl group, a butyl group or a hydroxyl group such as a hydroxyethyl group or a hydroxybutyl group. In addition, there can also be used a cyclohexyl group, a norbornel group, a cyclic vinyl having hydrogen or a carbonyl group in an aromatic ring or a cyclic structure thereof, an allyl ether, or a fluorine-containing vinyl ether or fluorine-containing allyl ether in which hydrogen of the above-mentioned functional group is partially or totally substituted by fluorine atoms.

Besides, it is possible to use with no particular limitation, as long as it is a vinyl ester, a vinylsilane, an olefin, a fluorine-containing olefin, a norbornene, a fluorine-containing norbornene compound or another compound containing a polymerizable unsaturated bond.

As the olefin, there can be exemplified ethylene, propylene, isobutene, cyclopentene, cyclohexene or the like, and as the fluorine-containing olefin, there can be exemplified vinyl fluoride, vinylidene fluoride, trifluoroethylene, chlorotrifluoroethylene, tetrafluoroethylene, hexafluoropropylene, hexafluoroisobutene, a cyclic olefin such as octafluorocyclopentene, or the like The norbornene compound or the fluorine-containing norbornene compound is a norbornene monomer having a mononuclear or multinuclear structure. In this case, it is a norbornene compound formed by the Diels-Alder addition reaction of an unsaturated compound such as a fluorine-containing olefin, allyl alcohol, fluorine-containing allyl alcohol, homoallyl alcohol, fluorine-containing homoallyl alcohol, acrylic acid, α-fluoroacrylic acid, α-trifluoromethylacrylic acid, methacrylic acid, all acrylic esters methacrylic esters, fluorine-containing acrylic esters and fluorine-containing methacrylic esters described in this specification, 2-(benzoyloxy)pentafluoropropane, 2-(methoxyethoxymethyloxy)pentafluoropropene, 2-(tetra-hydroxypyranyloxy) pentafluoropropene, 2-(benzoyloxy)trifluoroethylene or 2-(methoxymethyloxy)trifluoroethylene with cyclopentadiene or cyclohexadiene), and there can be exemplified 3-(5-bicyclo[2.2.1]heptene-2-yl)-1,1,1-trifluoro-2-(trifluoromethyl)-2-propanol or the like. The above-mentioned copolymerizable compounds may be used either alone or as a combination of two or more thereof.

Although there is no particular limitation on the copolymerization composition ratio, the ratio of the fluorine-containing compound of the invention is preferably selected between 10 mol % and 100 mol %. More preferably, it is from 30 mol % to 100 mol %, and less than 30 mol % results in failure to exhibit sufficient transparency and film forming properties, depending on the wavelength region of an application field.

A polymerization method of the polymer compound according to the invention is not particularly limited, as long as it is a method generally used. However, radical polymerization or ionic polymerization is preferred. In some cases, it is also possible to use coordinated anionic polymerization, living anionic polymerization, cationic polymerization, ring-opening metathesis polymerization or vinylene polymerization.

The radical polymerization is conducted by a known polymerization method such as bulk polymerization, solution polymerization, suspension polymerization or emulsion polymerization by any one of a batch-wise, half-continuous and continuous operations under the presence of a radical polymerization initiator or a radical initiating source.

Although the radical polymerization initiator is not particularly limited, examples thereof include are an azo compound, a peroxide compound and a redox compound. In particular, preferred are azobisbutyronitrile, t-butyl peroxypivalate, di-t-butyl peroxide, i-butyryl peroxide, lauroyl peroxide, succinic acid peroxide, dicinnamyl peroxide, di-n-propyl peroxydicarbonate, t-butyl peroxyallylmonocarbonate, benzoyl peroxide, hydrogen peroxide, ammonium persulfate and the like.

A reaction vessel which is used for the polymerization is not particularly limited. As a polymerization solvent, one which does not inhibit radical polymerization is preferred, and typical examples thereof include ester-based solvents such as ethyl acetate and n-butyl acetate, ketone-based solvents such as acetone and methyl isobutyl ketone, hydrocarbon-based solvents such as toluene and cyclohexane, alcohol-based solvents such as methanol, isopropyl alcohol and ethylene glycol monomethyl ether, and the like. Further, it is also possible to use various solvents such as water, an ether-based, cyclic ether-based, chlorofluorocarbon-based and aromatic solvents. These solvents can be used either alone or as a mixture of two or more thereof. Furthermore, a molecular weight modifier such as mercaptan may be used together. The reaction temperature of the polymerization reaction is appropriately changed depending on the radical polymerization initiator or the radical polymerization initiating source. It is usually preferably 20 to 200° C., and particularly preferably 30 to 140° C.

On the other hand, the ring-opening metathesis polymerization is only required to use a catalyst of a transition metal of the group IV, V, VI or VII under the presence of a cocatalyst, and to use a known method under the presence of a solvent.

Although the polymerization catalyst is not particularly limited, examples thereof include a Ti-based, V-based, Mo-based and W-based catalysts. In particular, preferred are titanium (IV) chloride, vanadium (IV) chloride, vanadium trisacetylacetonato, vanadium bisacetylacetonatodichloride, molybdenum (VI) chloride, tungsten (VI) chloride and the like. The amount of the polymerization catalyst is from 10 mol % to 0.001 mol %, and preferably from 1 mol % to 0.01 mol %, based on the monomer used.

The cocatalysts include an alkylaluminum, an alkyltin and the like. In particular, there can be exemplified aluminum cocatalysts such as trialkylaluminums such as trimethylaluminum, triethylaluminum, tripropylaluminum, triisopropylaluminum, triisobutylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum and trioctylaluminum, dialkylaluminum halides such as dimethylaluminum chloride, diethylaluminum chloride, diisopropylaluminum chloride and diisobutylaluminum chloride, monoalkylaluminum halides such as methylaluminum dichloride, ethylaluminum dichloride, ethylaluminum diiodide, propylaluminum dichloride, isopropylaluminum dichloride, butylaluminum dichloride and isobutylaluminum dichloride, and alkylaluminum sesquichlorides such as methylaluminum sesquichloride, ethylaluminum sesquichloride, propylaluminum sesquichloride and isobutylaluminum sesquichloride, tetra-n-butyltin, tetraphenyltin, triphenylchlorotin and the like. The amount of the cocatalyst is 100 equivalents or less, and preferably within the range of 30 equivalents or less, by molar ratio based on the transition metal catalyst.

Further, the polymerization solvent may be any, as long as it does not inhibit the polymerization reaction. As typical ones, there can be exemplified aromatic hydrocarbon-based solvents such as benzene, toluene, xylene, chlorobenzene and dichlorobenzene, hydrocarbon-based solvents such as hexane, heptane and cyclohexane, halogenated hydrocarbons such as carbon tetrachloride, chloroform, methylene chloride and 1,2-dichloroethane, and the like. These solvents can be used either alone or as a mixture of two or more thereof. The reaction temperature is usually preferably from −70 to 200° C., and particularly preferably from −30 to 60° C.

The vinylene polymerization is only required to use a catalyst of a group III transition metal such as iron, nickel, rhodium, palladium or platinum, or a catalyst of a group IVB to VIB metal such as zirconium, titanium, vanadium, chromium, molybdenum or tungsten, under the presence of a cocatalyst, and to use a known method under the presence of a solvent.

Although the polymerization catalyst is not particularly limited, particularly preferred examples thereof include group VIII transition metal compounds such as iron (II) chloride, iron (III) chloride, iron (II) bromide, iron (III) bromide, iron (II) acetate, iron (III) acetylacetonato, ferrocene, nickelocene, nickel (II) acetate, nickel bromide, nickel chloride, dichlorohexylnickel acetate, nickel lactate, nickel oxide, nickel tetrafluoroborate, bis(allyl)nickel, bis(cyclopentadienyl)nickel, nickel (II) hexafluoroacetylacetonatotetrahydrate, nickel (II) trifluoroacetylacetonatodihydrate, nickel (II) acetylacetonatotetrahydrate, rhodium (III) chloride, rhodium tris(triphenylphosphine)trichloride, palladium (II) bis(trifluoroacetate), palladium (II) bis(acetylacetonato), palladium (II) 2-ethylhexanoate, palladium (II) bromide, palladium (II) chloride, palladium (II) iodide, palladium (II) oxide, monoacetonitriletris(triphenylphosphine)palladium (II) tretrafluoroborate, tetrakis(acetonitrile) palladium (II) tetrafluoroborate, dichlorobis(acetonitrile) palladium (II), dichlorobis(triphenylphosphine)palladium (II), dichlorobis(benzonitrile)palladium (II), palladium acetylacetonato, palladium bis(acetonitrile)dichloride, palladium bis(dimethylsulfoxide)dichloride and platinum bis(triethylphosphine)hydrobromide, and group IVB to VIB transition metal compounds such as vanadium (IV) chloride, vanadium trisacetylacetonato, vanadium bisacetylacetonatodichloride, trimethoxy(pentamethylcyclopentadienyl)titanium (IV), bis(cyclopentadienyl)titanium dichloride and bis(cyclopentadienyl)zirconium dichloride. The catalyst amount is from 10 mol % to 0.001 mol %, and preferably from 1 mol % to 0.01 mol %, based on the monomer used.

The cocatalysts include an alkylaluminoxane, an alkylaluminum and the like. In particular, there can be exemplified methylaluminoxane (MAO), trialkylaluminums such as trimethylaluminum, triethylaluminum, tripropylaluminum, triisopropylaluminum, triisobutylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum and trioctylaluminum, dialkylaluminum halides such as dimethylaluminum chloride, diethylaluminum chloride, diisopropylaluminum chloride and diisobutylaluminum chloride, monoalkylaluminum halides such as methylaluminum dichloride, ethylaluminum dichloride, ethylaluminum diiodide, propylaluminum dichloride, isopropylaluminum dichloride, butylaluminum dichloride and isobutylaluminum dichloride, alkylaluminum sesquichlorides such as methylaluminum sesquichloride, ethylaluminum sesquichloride, propylaluminum sesquichloride and isobutylaluminum sesquichloride, and the like. In the case of methylaluminoxane, the cocatalyst amount is from 50 to 500 equivalents or less in terms of Al. In the case of other alkylaluminums, it is 100 equivalents or less, and preferably within the range of 30 equivalents or less, based on the transition metal catalyst.

The polymerization solvent may be any, as long as it does not inhibit the polymerization reaction. As typical ones, there can be exemplified aromatic hydrocarbon-based solvents such as benzene, toluene, xylene, chlorobenzene and dichlorobenzene, hydrocarbon-based solvents such as hexane, heptane and cyclohexane, halogenated hydrocarbon-based solvents such as carbon tetrachloride, chloroform, methylene chloride and 1,2-dichloroethane, dimethylformamide, N-methylpyrolidone, N-cyclohexylpyrolidone, and the like. These solvents can be used either alone or as a mixture of two or more thereof. The reaction temperature is usually preferably from −70 to 200° C., and particularly preferably from −40 to 80° C.

As a method for removing an organic solvent or water, a medium, from a solution or dispersion of the polymer compound according to the invention thus obtained, there can be utilized any known method. Examples thereof include a method such as reprecipitation and filtration, or heat distillation under reduced pressure.

For the polymer compound of the invention, it is appropriate to have a number average molecular weight usually of 1,000 to 100,000, and preferably ranging from 3,000 to 50,000.

Application fields according to the invention will be described below. In the invention, a coating application is basically used, and usually, the polymer compound of the invention is dissolved in an organic solvent and formed into a film, thereby being subjected to the application. Accordingly, the organic solvent used is not particularly limited, as long as the polymer compound is soluble therein. It is possible to use ketones such as acetone, methyl ethyl ketone, cyclohexanone, methyl isoamyl ketone and 2-heptanone, polyhydric alcohols and derivatives thereof such as ethylene glycol, ethylene glycol monoacetate, diethylene glycol, diethylene glycol monoacetate, propylene glycol, propylene glycol monoacetate, dipropylene glycol, and monomethyl ether, monoethyl ether, monopropyl ether, monobutyl ether or monophenyl ether of dipropylene glycol monoacetate, cyclic ethers such as dioxane, esters such as methyl lactate, ethyl lactate, methyl acetate, ethyl acetate, butyl acetate, methylpyruvate, ethyl pyruvate, methyl methoxypropionate and ethyl ethoxypropionate, aromatic solvents such as xylene and toluene, fluorine-containing solvents such as chlorofluorocarbon, an alternative for chlorofluorocarbon, a perfluoro compound and hexafluoroisopropyl alcohol, and terpene-based petroleum naphtha solvents or paraffinic solvents which are high-boiling weak solvents for the purpose of increasing coating properties, and the like. These may be used either alone or a mixture of two or more thereof.

A resist composition according to the invention is one containing both of a dissolution inhibitor of which solubility in an alkaline aqueous solution varies by the action of an acid and the polymer compound, or one in which the dissolution inhibitor is incorporated into the polymer compound. These are particularly suitable as positive type resist materials, and also suitable as positive type resist for 248-nm KrF or 193-nm ArF excimer lasers or for $F_2$ lasers in a vacuum ultraviolet region represented by 157 nm, electron beam resists and resists for X-rays. That is, the dissolution inhibitor of which solubility in an alkaline aqueous solution varies by the action of an acid is made so that at least one of hexafluorocarbinol groups becomes an acid labile group. However, it is usable with no particular limitation on the structure thereof. The commonly used acid labile group is the acid labile group described above, and a functional group which is severed with an acid. The polymer compound in which such a dissolution inhibitor is used is insoluble or slightly soluble in the alkaline aqueous solution before the irradiation of active energy rays, and hydrolyzed with an acid generated from an acid generator by the irradiation of the active energy rays, resulting in showing solubility in the alkaline aqueous solution.

There is no particular limitation on the acid generator used in the composition of the invention, and any one can be selected from acid generators used for chemically amplified resists to use. Examples of such acid generators include bissulfonyldiazomethanes, nitrobenzyl derivatives, onium salts, halogen-containing triazine compounds, cyano group-containing oximesulfonate compounds, other oximesulfonate compounds and the like. These acid generators may be used either alone or as a combination of two or more thereof. Further, the content thereof is usually selected within the range of 0.5 to 20 parts by weight based on 100 parts by weight of the polymer compound. When this amount is less than 0.5 part by weight, image forming properties are insufficient. Exceeding 20 parts by weight results in difficulty forming a homogeneous solution, thus showing a tendency of storage stability to deteriorate.

As a method for use of the resist of the invention, there is used a pattern forming process in a conventional photoresist technique. In order to suitably perform the process, first, a solution of the resist composition is applied onto a support such as a silicon wafer with a spinner or the like, followed by drying to form a photosensitive layer. This is irradiated with excimer laser light by an exposure apparatus through a desired mask pattern, followed by heating. Then, this is subjected to a development treatment by using a developing solution, for example, an alkaline aqueous solution such as a 0.1–10 wt % aqueous solution of tetramethylammonium hydroxide. A pattern faithful to the mask pattern can be obtained by this forming process.

Depending on the application fields of the invention, it is possible to incorporate miscible additives as needed, for example, various additives such as an additional resin, quencher, plasticizer, stabilizer, coloring agent, surfactant, tackifier, leveling agent, deforming agent, compatibility enhancing agent, adhesion enhancing agent, and antioxidant.

EXAMPLES

The present invention will be illustrated in greater detail with reference to the following examples, but the invention should not be construed as being limited thereto.

Example 1

Synthesis of Compound (2)

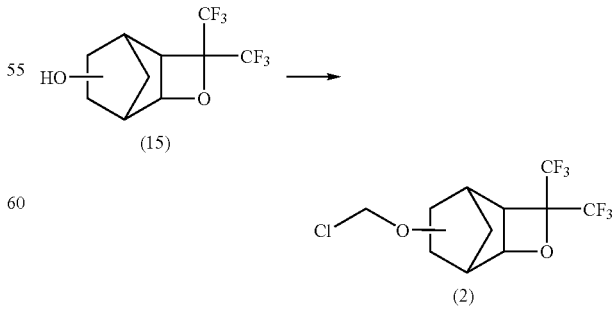

Compound (15) (14.2 g), paraformaldehyde (2.9 g) and chloroform (140 ml) were put in a 300-ml three-necked flask. Hydrogen chloride was blown therein until compound (15) had been consumed while maintaining the internal temperature at 10° C. or lower in an ice-water bath. After the termination of the reaction, a reaction solution was washed with a saturated sodium bicarbonate solution and a saturated saline solution, dried, filtered, and concentrated to obtain a crude product (20.1 g). This was refined by distillation under reduced pressure to obtain compound (2) (9.5 g, yield: 57.0%).

Physical Property Data
MS (EI): m/e 324 (M$^+$), 289 (M$^+$-Cl), 259 (M$^+$-OCH$_2$Cl)
IR: The spectrum is shown in FIG. 1.

Example 2

Synthesis of Compound (5)

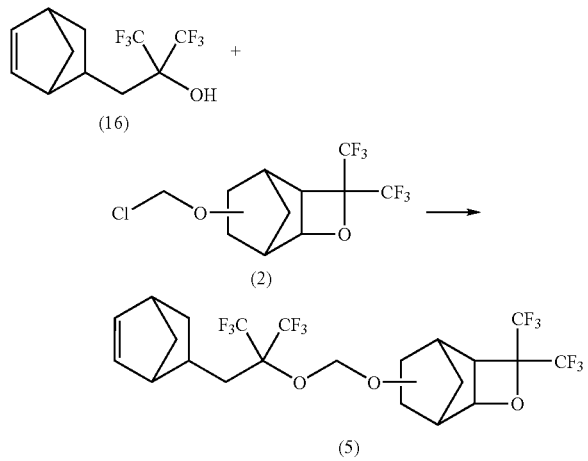

Compound (16) (42 mg), tetrabutylammonium iodide (5 mg) and THF (5 ml) were put in a 10-ml flask equipped with a reflux condenser, a dropping funnel, a thermometer and a stirrer, and cooled in an ice water bath. Sodium hydride (8 mg) was added under nitrogen gas flow, and stirred until hydrogen ceased to be produced. Compound (2) (50 mg) was put in the dropping funnel, and added dropwise in such a manner that the temperature of a reaction solution did not exceed 30° C. After the termination of dropping, stirring was further continued at room temperature for 0.5 hour. After the termination of the reaction, a reaction solution was washed with a saturated sodium bicarbonate solution and a saturated saline solution, dried, filtered, and concentrated to obtain compound (5) (77 mg, yield: 89%).

Physical Property Data
MS (EI): m/e 562(M$^+$), 287, 275, 273, 259

Example 3

Synthesis of Compound (18)

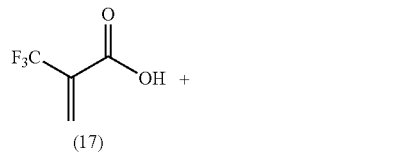

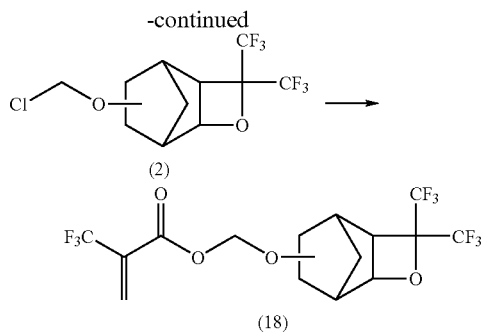

Compound (17) (3.77 g), triethylamine (4.6 ml) and THF (40 ml) were put in a 50-ml three-necked flask, and compound (2) was added dropwise at room temperature. White crystals were immediately deposited. After it was confirmed that compound (2) had been consumed, a reaction solution was subjected to suction filtration. A filtrate was washed with a saturated sodium bicarbonate solution and a saturated saline solution, dried, filtered, and concentrated to obtain a crude product (10.96 g). This was refined by distillation under reduced pressure to obtain compound (18) (6.32 g, yield: 55.0%).

Figure 2:
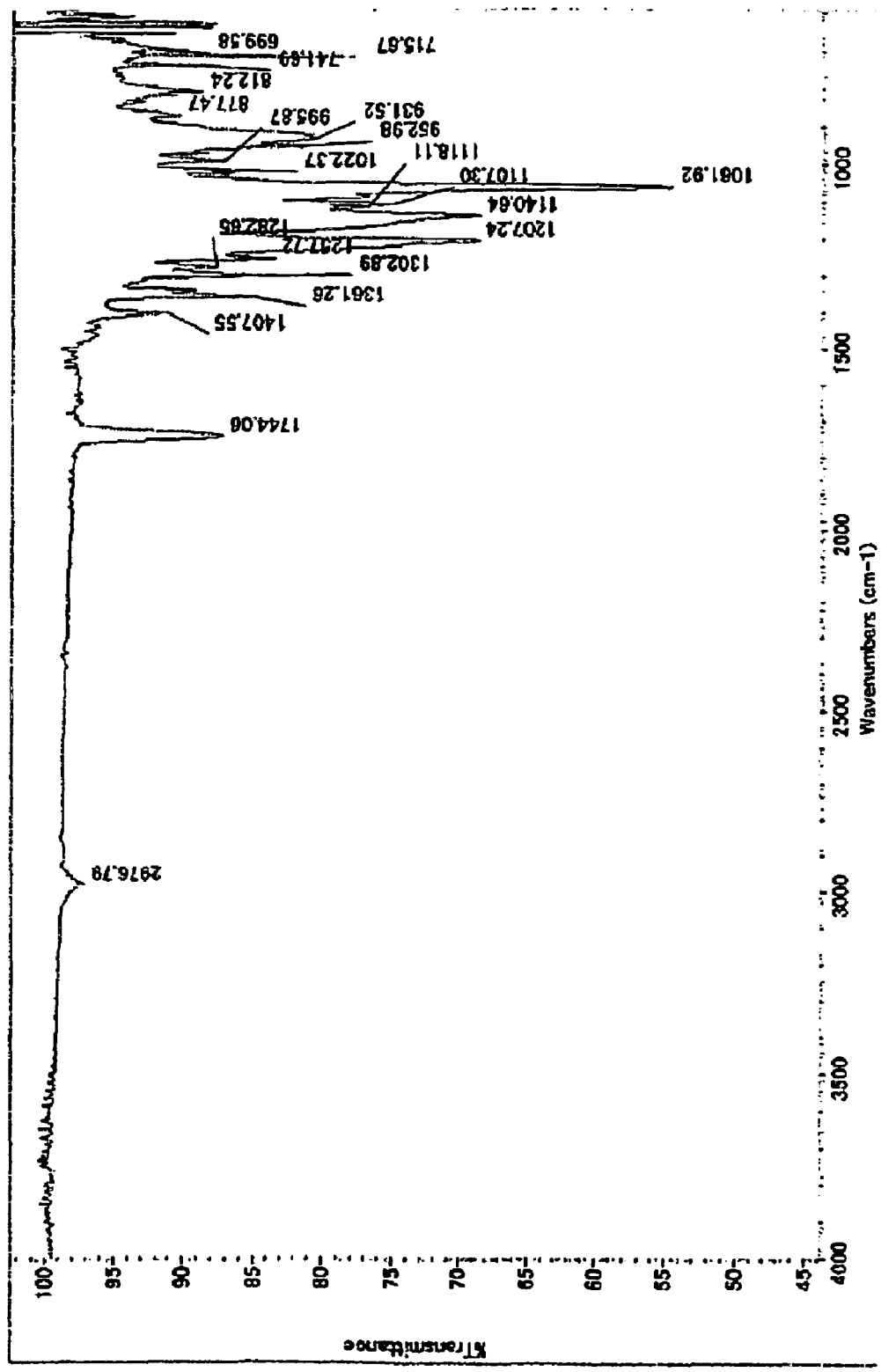
FIG. 2 is a diagram showing an IR spectrum as physical property data of Example 3.

Physical Property Data
MS (EI): m/e 428(M$^+$), 259(M$^+$-OCH$_2$O$_2$CCH$_2$CCF$_3$)
IR: The spectrum is shown in FIG. 2.

Example 4

Synthesis of Compound (20)

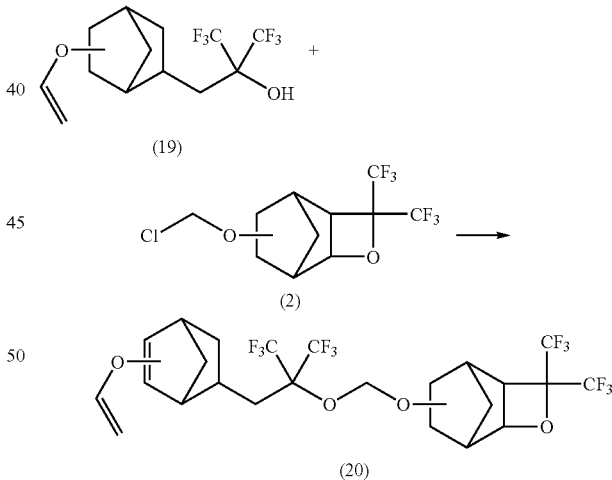

Compound (19) (56 mg), tetrabutylammonium iodide (5 mg) and THF (5 ml) were put in a 10-ml flask equipped with a reflux condenser, a dropping funnel, a thermometer and a stirrer, and cooled in an ice water bath. Sodium hydride (6 mg) was added under nitrogen gas flow, and stirred until hydrogen ceased to be produced. Compound (2) (50 mg) was put in the dropping funnel, and added dropwise in such a manner that the temperature of a reaction solution did not exceed 30° C. After the termination of dropping, stirring was further continued at room temperature for 0.5 hour. After the termination of the reaction, a reaction solution was washed with a saturated sodium bicarbonate solution and a saturated saline solution, dried, filtered, and concentrated to obtain compound (20) (71 mg, yield: 76%).

Physical Property Data

MS (EI): m/e 606(M$^+$), 331, 289, 287, 275, 259, 241

Example 5

Synthesis of Copolymer of Compound (20) and Compound (21)

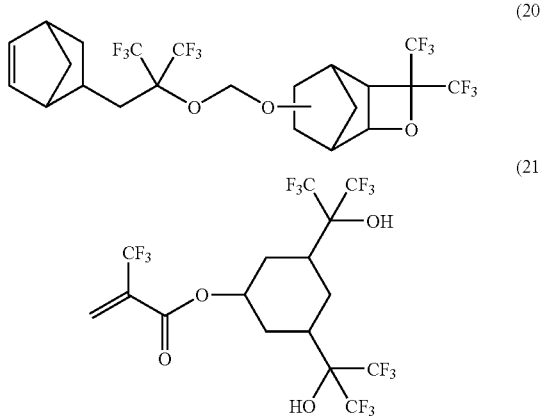

Compound (20) (5.6 g), compound (21) (5.5 g), n-butyl acetate (11.1 ml) and AIBN (150 mg) were put in a flask equipped with a reflux condenser and stirrer under nitrogen gas flow, and stirred for 20 hours with heating in an oil bath of 60° C. After the termination of the reaction, a reaction solution was poured into n-hexane (100 ml), followed by stirring, and a precipitate formed was taken out by filtration. This was vacuum dried at 50° C. for 18 hours to obtain a white solid polymer (polymer 1) (8.1 g, Mw=17,000, Mw/Mn=1.5). The structure thereof was confirmed by NMR, and the molecular weight was determined from gel permeation chromatography (GPC, standard polystyrene).

Example 6

Synthesis of Copolymer of Compound (16) and Compound (21), and HFIP Protection Reaction of the Copolymer

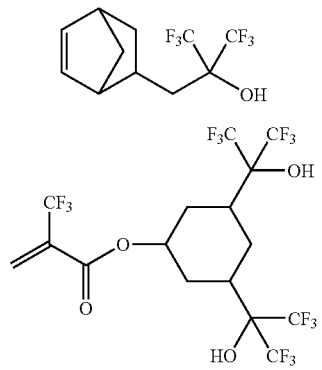

Compound (16) (5.6 g), compound (21) (5.5 g), n-butyl acetate (11.1 ml) and AIBN (150 mg) were put in a flask equipped with a reflux condenser and stirrer under nitrogen gas flow, and stirred for 20 hours with heating in an oil bath of 60° C. After the termination of the reaction, a reaction solution was poured into n-hexane (100 ml), followed by stirring, and a precipitate formed was taken out by filtration. This was vacuum dried at 50° C. for 18 hours to obtain a white solid polymer (8.1 g, Mw=16,800, Mw/Mn=1.5).

Subsequently, the polymer synthesized above (4.0 g), tetrabutylammonium iodide (0.1 g) and THF (25 ml) were put in a 100-ml three-necked flask equipped with a reflux condenser, a dropping funnel, a thermometer and a stirrer, and cooled in an ice water bath. Sodium hydride (0.4 g) was added under nitrogen gas flow, and stirred until hydrogen ceased to be produced. Compound (2) (1.0 g) was put in the dropping funnel, and added dropwise in such a manner that the temperature of a reaction solution did not exceed 30° C. Stirring was further continued at room temperature for 1 hour. After the termination of the reaction, a reaction solution was poured into water, and a precipitate formed was taken out by filtration. It was dissolved in acetone (5 ml), and the resulting solution was poured into n-hexane (50 ml), followed by stirring. A precipitate formed was taken out by filtration. This was vacuum dried at 50° C. for 18 hours to obtain a white solid polymer (polymer 2) (2.4 g, Mw=18,200, Mw/Mn=1.5, HFIP protection ratio: 53%). The structure thereof was confirmed by NMR, and the molecular weight was determined from gel permeation chromatography (GPC, standard polystyrene).

Example 7

Synthesis of Copolymer of Compound (20) and Compound (21)

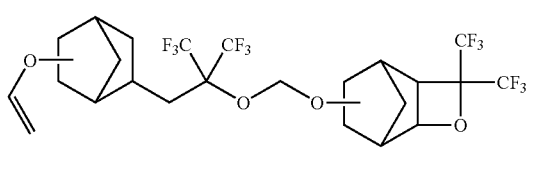

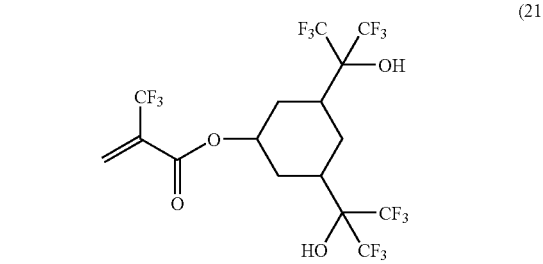

Compound (20) (6.6 g), compound (21) (5.5 g), n-butyl acetate (12.1 ml) and AIBN (150 mg) were put in a flask equipped with a reflux condenser and stirrer under nitrogen gas flow, and stirred for 20 hours with heating in an oil bath of 60° C. After the termination of the reaction, a reaction solution was poured into n-hexane (200 ml), followed by stirring, and a precipitate formed was taken out by filtration.

This was vacuum dried at 50° C. for 18 hours to obtain a white solid polymer (polymer 3) (8.4 g, Mw=132,600, Mw/Mn=1.9). The structure thereof was confirmed by NMR, and the molecular weight was determined from gel permeation chromatography (GPC, standard polystyrene).

Example 8

Synthesis of Copolymer of Compound (21) and Compound (22), and HFIP Protection Reaction of the Copolymer

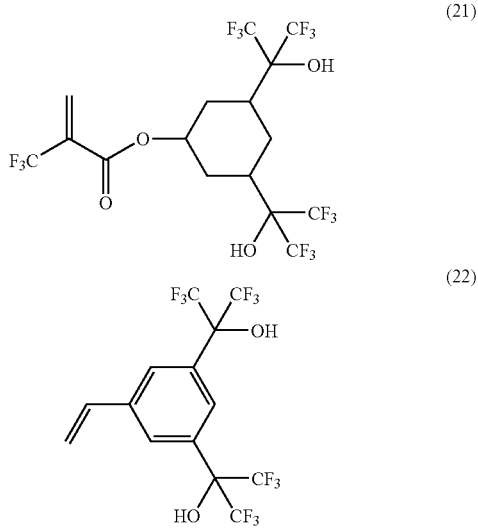

Compound (21) (5.0 g), compound (22) (7.0 g), n-butyl acetate (13.0 ml) and AIBN (200 mg) were put in a flask equipped with a reflux condenser and stirrer under nitrogen gas flow, and stirred for 20 hours with heating in an oil bath of 60° C. After the termination of the reaction, a reaction solution was poured into n-hexane (200 ml), followed by stirring, and a precipitate formed was taken out by filtration. This was vacuum dried at 50° C. for 18 hours to obtain a white solid polymer (10.4 g, Mw=13,600, Mw/Mn=1.7).

Subsequently, the polymer synthesized above (7.0 g), tetrabutylammonium iodide (0.1 g) and THF (35 ml) were put in a 100-ml three-necked flask equipped with a reflux condenser, a dropping funnel, a thermometer and a stirrer, and cooled in an ice water bath. Sodium hydride (0.8 g) was added under nitrogen gas flow, and stirred until hydrogen ceased to be produced. Compound (2) (2.0 g) was put in the dropping funnel, and added dropwise in such a manner that the temperature of a reaction solution did not exceed 30° C. Stirring was further continued at room temperature for 1 hour. After the termination of the reaction, a reaction solution was poured into water, and a precipitate formed was taken out by filtration. It was dissolved in acetone (5 ml), and the resulting solution was poured into n-hexane (100 ml), followed by stirring. A precipitate formed was taken out by filtration. This was vacuum dried at 50° C. for 18 hours to obtain a white solid polymer (polymer 4) (4.9 g, Mw=14,700, Mw/Mn=1.7, HFIP protection ratio: 49%). The structure thereof was confirmed by NMR, and the molecular weight was determined from gel permeation chromatography (GPC, standard polystyrene).

Example 9

Synthesis of Copolymer of Compound (16) and Compound (18)

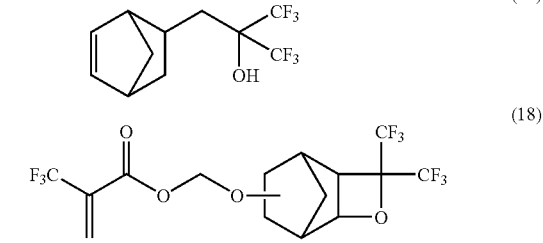

BTHB-NB (16) (2.8 g), compound (18) (4.8 g), n-butyl acetate (7.1 g) and AIBN (100 mg) were put in a flask equipped with a reflux condenser and stirrer under nitrogen gas flow, and stirred for 20 hours with heating in an oil bath of 60° C. After the termination of the reaction, a reaction solution was poured into n-hexane (400 ml), followed by stirring, and a precipitate formed was taken out by filtration. This was vacuum dried at 50° C. for 18 hours to obtain a white solid polymer (polymer 5) (5.1 g, Mw=12,100, Mw/Mn=1.5). The structure thereof was confirmed by NMR, and the molecular weight was determined from gel permeation chromatography (GPC, standard polystyrene).

Example 10

The polymer compounds of Examples 5 to 9 were each dissolved in propylene glycol methyl acetate so as to be adjusted to a solid content of 14%. Further, as an acid generator, triphenylsulfonium triflate (TPS105) manufactured by Midori Kagaku Co., Ltd. was dissolved in an amount of 2 parts by weight per 100 parts by weight of each polymer compound, thereby preparing two kinds of resist solutions. These were applied by spin coating, and the light transmittance at a film thickness of 100 nanometers was measured at a wavelength of 157 nm. As a result, it was found to be 68%, 71%, 69%, 51% and 61%, respectively, for Examples 5, 6, 7, 8 and 9, which exhibited high transparency in a vacuum ultraviolet wavelength region.

Then, after all resist solutions were filtered through a membrane filter having a pore size of 0.2 μm, each composition solution was applied onto a silicon wafer by spin coating to obtain a resist film having a film thickness of 250 nanometers. After the film was prebaked at 120° C., it was exposed to an ultraviolet ray through a photomask, and then, subjected to post exposure baking at 130° C. Subsequently, it was developed at 23° C. for 1 minute, using a 2.38 wt % aqueous solution of tetramethylammonium hydroxide. As a result, resist patterns were obtained from all resist solutions, and poor adhesion defects to substrates, poor film forming defects, development defects poor etching resistance defects were also scarcely observed.

While the present invention has been described in detail with reference to specific embodiments thereof, it will be apparent to one skilled in the art that various changes and modifications can be made therein without departing from the spirit and scope thereof.

The present application is based on Japanese Patent Application No. 2003-272269 filed Jul. 9, 2003, and the contents thereof are incorporated herein by reference.

INDUSTRIAL APPLICABILITY

The invention provides a novel fluorine-containing cyclic compound, fluorine-containing polymerizable monomer and fluorine-containing polymer compound, and the polymer compound synthesized using the novel fluorine-containing cyclic compound is suitable for a resist material having high transparency in a wide wavelength region from an ultraviolet region to a near-infrared light region, high adhesion to a substrate, film forming properties, high etching resistance and a high glass transition point at once, particularly for a photoresist material in a vacuum ultraviolet wavelength region. Further, a pattern forming process using the same is suitable for the formation of a high-resolution pattern form.

The invention claimed is:

1. A fluorine-containing cyclic compound represented by general formula (1):

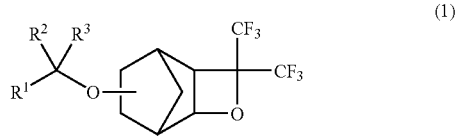

wherein $R^1$ represents a halogen atom, and $R^2$ and $R^3$ each represents hydrogen or a hydrocarbon group, the hydrocarbon group, which may contain a halogen atom, an oxygen atom, a nitrogen atom or a sulfur atom, being a straight-chain, branched or cyclic hydrocarbon group having 1 to 25 carbon atoms or an aromatic hydrocarbon group.

2. The fluorine-containing cyclic compound according to claim 1, which is represented by structural formula (2):

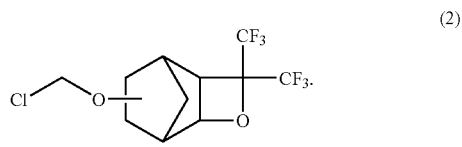

3. A fluorine-containing cyclic compound derived from the fluorine-containing cyclic compound according to claim 1, which is represented by general formula (3):

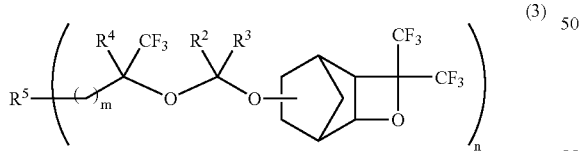

wherein $R^2$ and $R^3$ each represents hydrogen or a hydrocarbon group, the hydrocarbon group, which may contain a halogen atom, an oxygen atom, a nitrogen atom or a sulfur atom, being a straight-chain, branched or cyclic hydrocarbon group having 1 to 25 carbon atoms or an aromatic hydrocarbon group; $R^4$ and $R^5$ each represents hydrogen or a hydrocarbon group, the hydrocarbon group, which may contain a halogen atom, an oxygen atom, a nitrogen atom, a sulfur atom, a carbonyl bond or a double bond, being a straight-chain, branched or cyclic hydrocarbon group having 1 to 25 carbon atoms or an aromatic hydrocarbon group, and further, $R^5$ may be bonded to any polymer chain; n represents 1 to 5; and m represents 0 to 5.

4. A fluorine-containing cyclic compound derived from the fluorine-containing cyclic compound according to claim 1, which is represented by general formula (4):

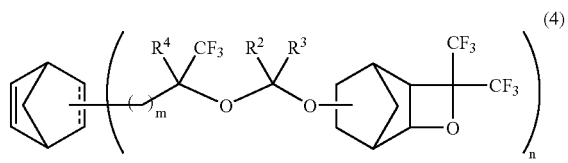

wherein $R^2$ and $R^3$ each represents hydrogen or a hydrocarbon group, the hydrocarbon group, which may contain a halogen atom, an oxygen atom, a nitrogen atom or a sulfur atom, being a straight-chain, branched or cyclic hydrocarbon group having 1 to 25 carbon atoms or an aromatic hydrocarbon group; $R^4$ represents hydrogen or a hydrocarbon group, the hydrocarbon group, which may contain a halogen atom, an oxygen atom, a nitrogen atom, a sulfur atom or a carbonyl bond, being a straight-chain, branched or cyclic hydrocarbon group having 1 to 25 carbon atoms or an aromatic hydrocarbon group; n represents 1 to 5; and m represents 0 to 5.

5. A fluorine-containing cyclic compound represented by structural formula (5):

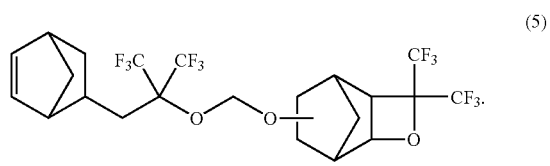

6. A fluorine-containing cyclic compound derived from the fluorine-containing cyclic compound according to claim 1, which is represented by general formula (6):

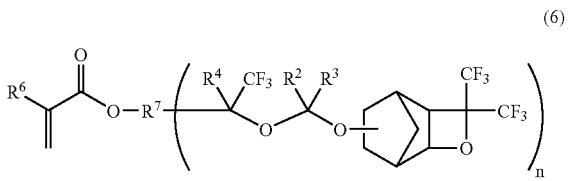

wherein $R^2$ and $R^3$ each represents hydrogen or a hydrocarbon group, the hydrocarbon group, which may contain a halogen atom, an oxygen atom, a nitrogen atom or a sulfur atom, being a straight-chain, branched or cyclic hydrocarbon group having 1 to 25 carbon atoms or an aromatic hydrocarbon group; $R^4$ represents hydrogen or a hydrocarbon group, the hydrocarbon group, which may contain a halogen atom, an oxygen atom, a nitrogen atom, a sulfur atom or a carbonyl bond, being a straight-chain, branched or cyclic hydrocarbon group having 1 to 25 carbon atoms or an aromatic hydrocarbon group; $R^6$ represents hydrogen, a fluorine atom, a halogen atom, an alkyl group or a halogenated alkyl group; n represents 1 to 5; $R^7$ is a methylene group, a methine group, or a cyclic hydrocarbon group or aromatic hydrocarbon group represented by structural formulas (7) to (9), which may contain a halogen atom, an oxygen atom, a nitrogen atom or a sulfur atom as a substituent group thereof; and m represents 0 to 5 in structural formula (7).

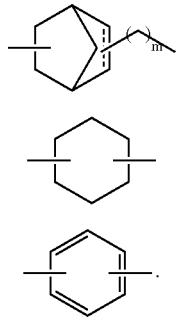

7. A fluorine-containing cyclic compound derived from the fluorine-containing cyclic compound according to claim 1, which is represented by general formula (10):

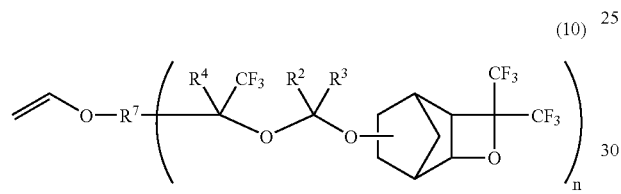

wherein $R^2$ and $R^3$ each represents hydrogen or a hydrocarbon group, the hydrocarbon group, which may contain a halogen atom, an oxygen atom, a nitrogen atom or a sulfur atom, being a straight-chain, branched or cyclic hydrocarbon group having 1 to 25 carbon atoms or an aromatic hydrocarbon group; $R^4$ represents hydrogen or a hydrocarbon group, the hydrocarbon group, which may contain a halogen atom, an oxygen atom, a nitrogen atom, a sulfur atom or a carbonyl bond, being a straight-chain, branched or cyclic hydrocarbon group having 1 to 25 carbon atoms or an aromatic hydrocarbon group; n represents 1 to 5; $R^7$ is a methylene group, a methine group, or a cyclic hydrocarbon group or aromatic hydrocarbon group represented by structural formula (7) to (9), which may contain a halogen atom, an oxygen atom, a nitrogen atom or a sulfur atom as a substituent group thereof; and m represents 0 to 5 in structural formula (7)

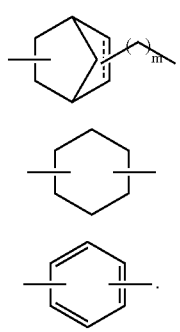

8. A fluorine-containing cyclic compound derived from the fluorine-containing cyclic compound according to claim 1, which is represented by general formula (11):

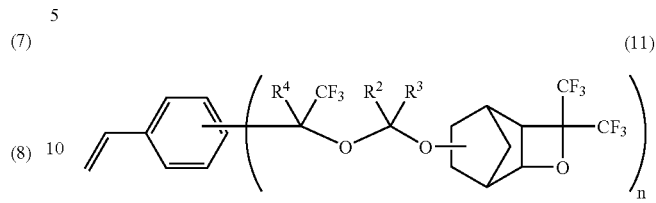

wherein $R^2$ and $R^3$ each represents hydrogen or a hydrocarbon group, the hydrocarbon group, which may contain a halogen atom, an oxygen atom, a nitrogen atom or a sulfur atom, being a straight-chain, branched or cyclic hydrocarbon group having 1 to 25 carbon atoms or an aromatic hydrocarbon group; $R^4$ represents hydrogen or a hydrocarbon group, the hydrocarbon group, which may contain a halogen atom, an oxygen atom, a nitrogen atom, a sulfur atom or a carbonyl bond, being a straight-chain, branched or cyclic hydrocarbon group having 1 to 25 carbon atoms or an aromatic hydrocarbon group; n represents 1 to 5.

9. A fluorine-containing cyclic compound derived from the fluorine-containing cyclic compound according to claim 1, which is represented by general formula (12):

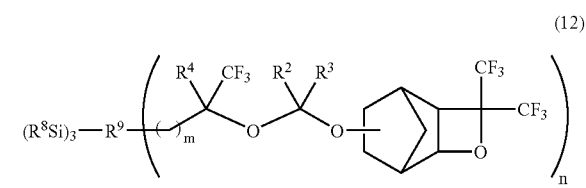

wherein $R^2$ and $R^3$ each represents hydrogen or a hydrocarbon group, the hydrocarbon group, which may contain a halogen atom, an oxygen atom, a nitrogen atom or a sulfur atom, being a straight-chain, branched or cyclic hydrocarbon group having 1 to 25 carbon atoms or an aromatic hydrocarbon group; $R^4$ represents hydrogen or a hydrocarbon group, the hydrocarbon group, which may contain a halogen atom, an oxygen atom, a nitrogen atom, a sulfur atom or a carbonyl bond, being a straight-chain, branched or cyclic hydrocarbon group having 1 to 25 carbon atoms or an aromatic hydrocarbon group; $R^8$ represents a halogen atom or an alkoxy group; n represents 1 to 5, and m represents 0 to 5; and $R^9$ is a cyclic hydrocarbon group represented by structural formulas (7) and (8) or an aromatic hydrocarbon group, which may contain a halogen atom, an oxygen atom, a nitrogen atom or a sulfur atom as a substituent group thereof.

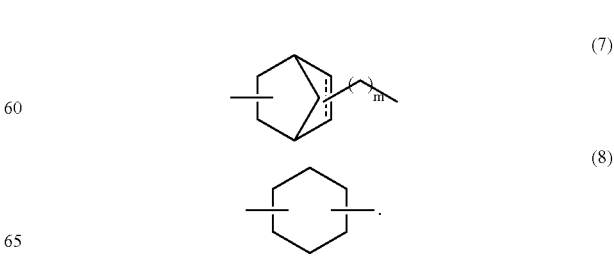

10. A fluorine-containing cyclic compound derived from the fluorine-containing cyclic compound according to claim 1, which is represented by general formula (13):

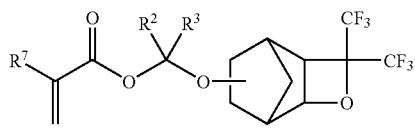

(13)

wherein $R^2$ and $R^3$ each represents hydrogen or a hydrocarbon group, the hydrocarbon group, which may contain a halogen atom, an oxygen atom, a nitrogen atom or a sulfur atom, being a straight-chain, branched or cyclic hydrocarbon group having 1 to 25 carbon atoms or an aromatic hydrocarbon group; and $R^7$ represents hydrogen, a fluorine atom, a halogen atom, an alkyl group or a halogenated alkyl group.

11. A fluorine-containing cyclic compound represented by structural formula (14):

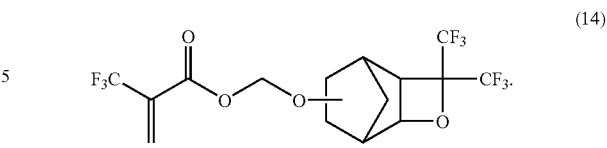

(14)

12. A fluorine-containing polymer compound obtained by polymerization or copolymerization using the fluorine-containing cyclic compound according to claim 3.

13. A fluorine-containing polymer obtained by reacting a polymer containing one or more functional groups selected from a carboxyl group, a hydroxyl group, a hexafluorocarbinol group, an amino group and a sulfonic acid with the fluorine-containing cyclic compound according to claim 1.

14. A resist material using the fluorine-containing polymer compound according to claim 12 or 13.

15. A pattering process using the resist material according to claim 14.

* * * * *